US005790673A

United States Patent [19]

Gossman

[11] Patent Number: 5,790,673

[45] Date of Patent: Aug. 4, 1998

[54] ACTIVE ACOUSTICAL CONTROLLED ENCLOSURE

[75] Inventor: William E. Gossman, Oakton, Va.

[73] Assignee: Noise Cancellation Technologies, Inc., Linthicum, Md.

[21] Appl. No.: 835,009

[22] Filed: Apr. 9, 1997

Related U.S. Application Data

[63] Continuation of Ser. No. 347,395, filed as PCT/US92/04574, Jun. 10, 1992, published as WO93/25879, Dec. 23, 1993.

[51] Int. Cl.[6] .............................. A61F 11/06; H03B 29/00

[52] U.S. Cl. ........................ 381/71.1; 381/71.2; 381/71.7; 381/71.11

[58] Field of Search ............................... 381/71.1, 86, 94, 381/72, 71.2, 71.7, 71.11

[56] References Cited

U.S. PATENT DOCUMENTS

| | | | |
|---|---|---|---|
| 5,018,203 | 5/1991 | Sawyers et al. | 381/71 |
| 5,091,953 | 2/1992 | Tretter . | |
| 5,097,923 | 3/1992 | Ziegler et al. | 381/71 |

FOREIGN PATENT DOCUMENTS

| | | | |
|---|---|---|---|
| 0272299 | 12/1991 | Japan | 381/71 |

*Primary Examiner*—Curtis A. Kuntz
*Assistant Examiner*—Duc Nguyen

[57] ABSTRACT

A system and method for using active algorithmically controlled sensing (1*a*, 1*b*) and speaker (2*a*, 2*b*) for controlling noise from a distributed noise source (5) within an enclosure (6) with a multiple input, multiple output controller (7).

12 Claims, 7 Drawing Sheets

ACTIVE ACOUSTICAL CONTROLLED ENCLOSURE

This is a Continuation of application Ser. No.: 08/347,395, filed as PCT/US92/04574, Jun. 10, 1992, published as WO93/25879, Dec. 23, 1993.

This invention relates to providing an enclosure around a distributed noise source and employing acoustical control means to maximize transmission loss within the enclosure.

BACKGROUND

Building a high transmission loss enclosure around a distributed noise source is a common method of reducing the sound radiation from the source. As is also well-known, typical enclosures perform well only at high frequencies, or, are thick and heavy if they perform well at low frequencies. The use of an active, acoustically controlled enclosure to perform the same function has been suggested. The suggestion is that good noise reduction could be achieved by placing acoustic sources in a "box" around the noise source with a sensing microphone in the box, or at an opening. This approach is not optimal in that it cannot address the effects of the "control" sound field on the structural radiation of the "box". This term is often described as control spillover. An example of this occurs when active reduction of the sound field in the box causes an unanticipated excitation of radiating structural modes of the box.

Additionally boxes using only "passive" means such as padding or layering have been used without much success.

Accordingly, it is an object of the current invention to improve upon current implementations of active, acoustically controlled enclosures by addressing both structural radiation as well as direct source radiation from openings in the "box".

This is accomplished through proper placement of the error sensors as well as the type of control system used.

An additional object of the present invention is to allow for openings (i.e. for air flow) in the box while still allowing active control. This is accomplished by designing the openings of the box to have a high acoustical impedance at the disturbance frequencies. This will allow active control, and air flow into the box, and allow for smaller loudspeakers to be used.

These and other objects of the invention will become apparent when reference is had to the accompanying drawings in which FIG. 1 depicts a distributed noise source with an enclosure with an opening.

Figure 5A:
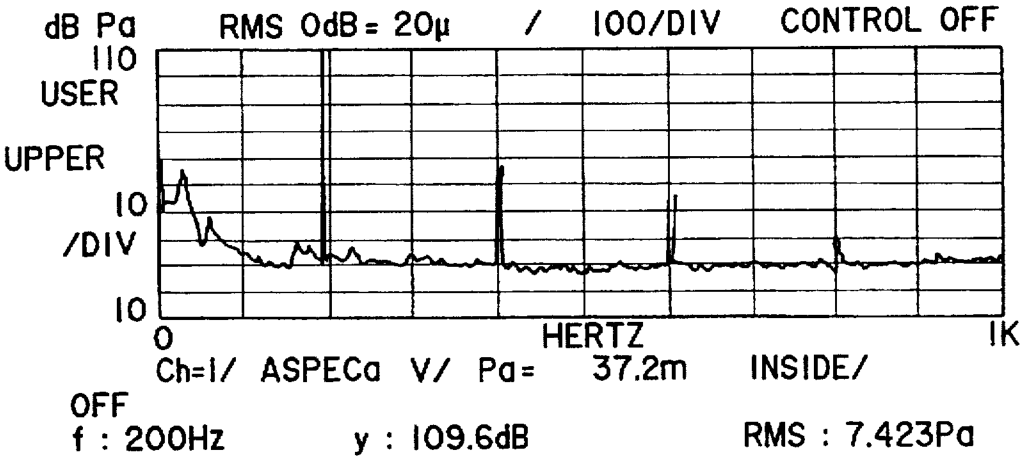
Figure 5B:
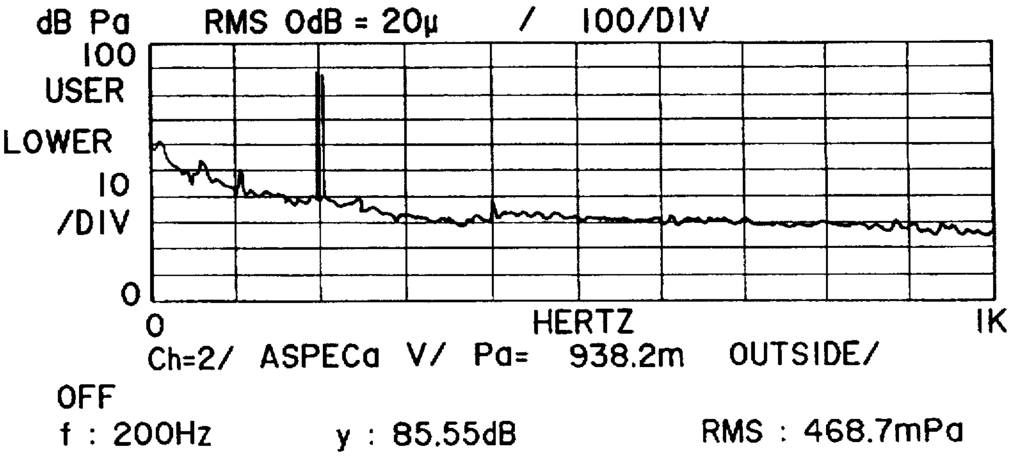

FIG. 5 is a plot of the Spectrum of sound pressure level (SPL) inside (upper plot) and outside (lower plot) a mockup of the watercraft. Acoustic source is two 6-inch loudspeakers driven with a 200 Hz tone at a level of 110 dB inside the engine compartment with control off. The controller is off for this measurement.

Figure 6A:
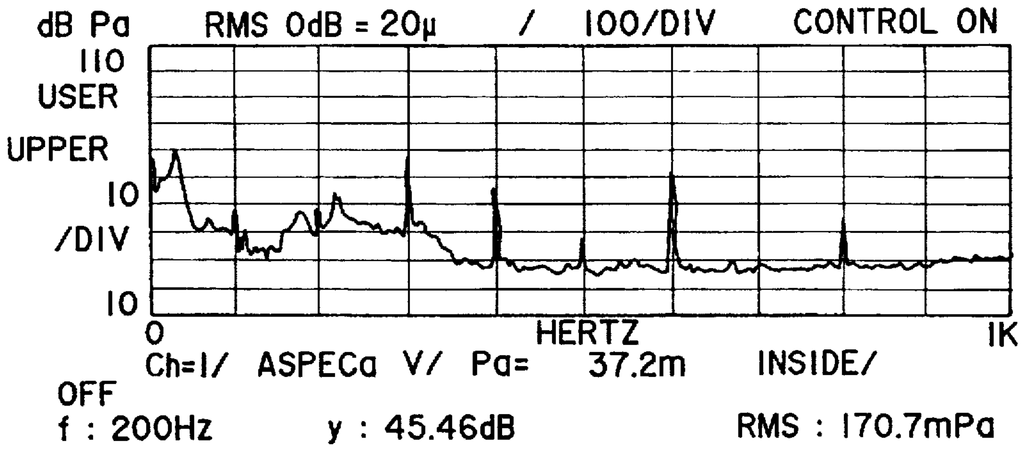
Figure 6B:
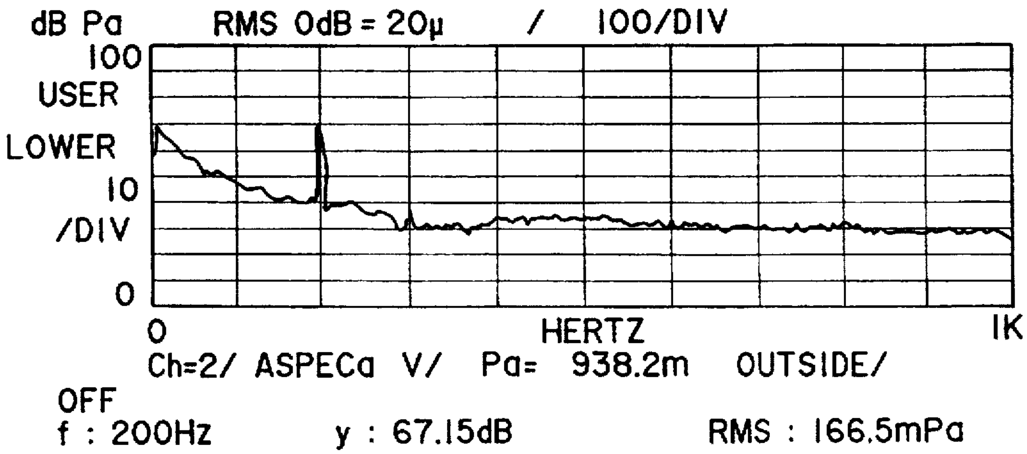

FIG. 6 is a plot of the spectrum of sound pressure level (SPL) inside (upper plot) and outside (lower plot) a mockup of the watercraft. Acoustic source is two 6-inch loudspeakers driven with a 200 Hz tone at a level of 110 dB inside the engine compartment with control off. The controller is on for this measurement.

Figure 7:
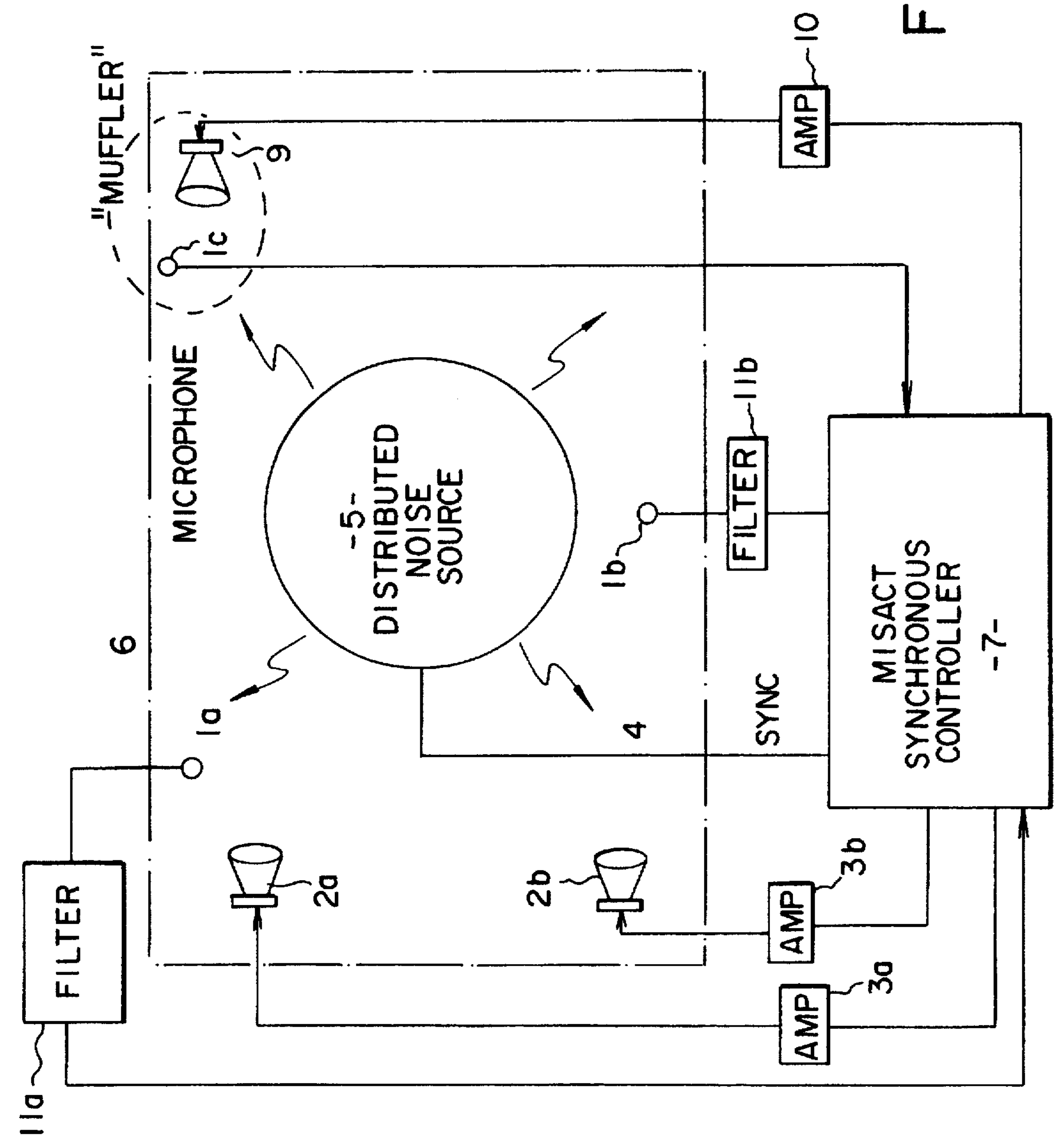

FIG. 7 depicts an enclosure that has no apertures, according to an aspect of the present invention.

DESCRIPTION OF INVENTION

Figure 1:
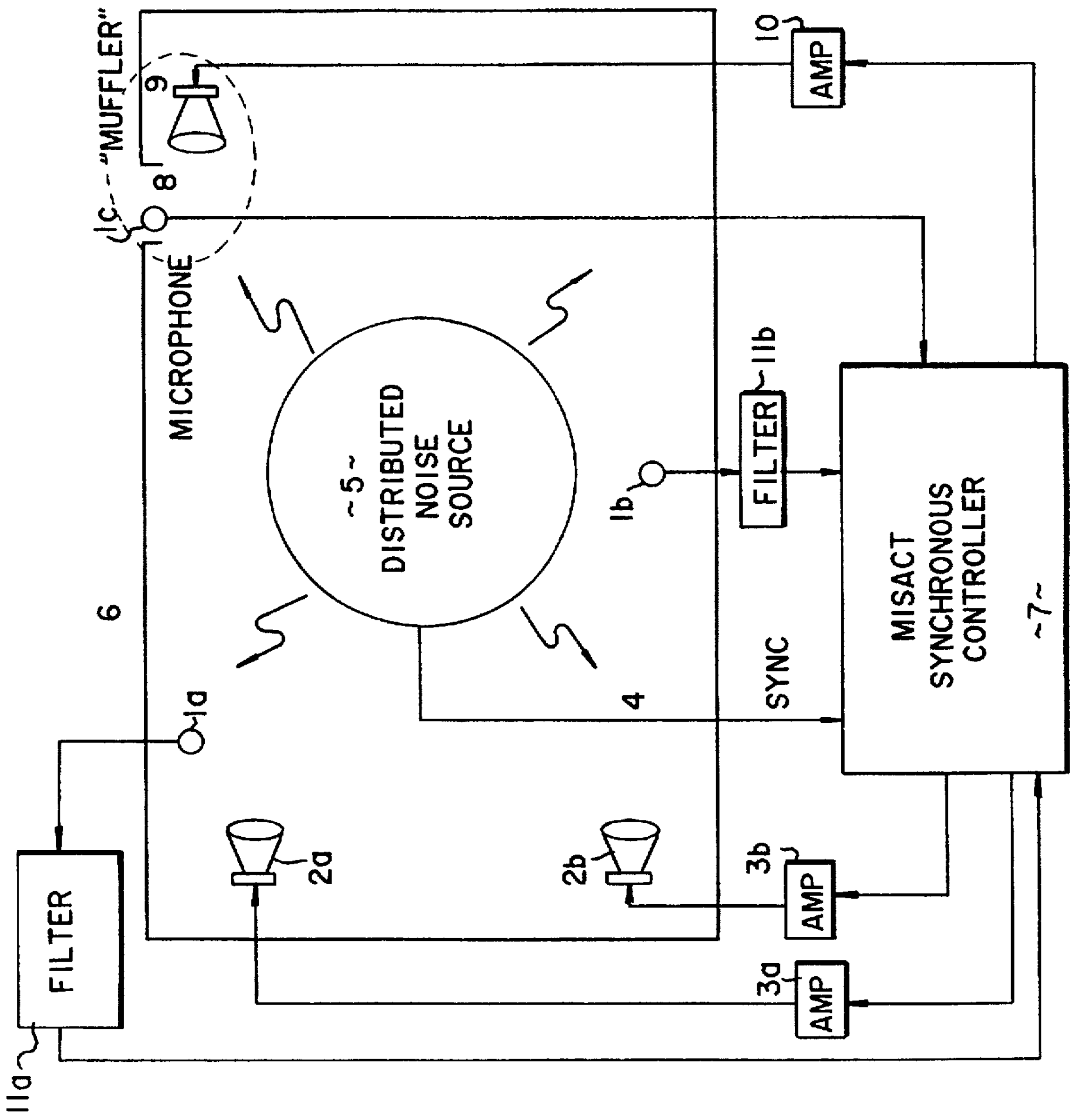

The object of this invention is to provide an enclosure around a distributed noise source. The enclosure utilizes acoustical control means to maximize transmission loss "across" all transmission paths. In FIG. 1, the transmission paths, shown as squigley lines, pass through either the structure of the enclosure or through openings therein.

Airborne Paths Only

It is well known, such as shown in U.S. Pat. No. 5,097,923, hereby incorporated by reference, that a compact acoustical source, such as an opening in the box, can be controlled with a number of loudspeakers preferably driven in phase to use a single input, single output (SISO) controller which is controlled by an adaptive noise canceling algorithm such as that disclosed in U.S. Pat. No. 5,091,953 which is hereby incorporated by reference herein. Such a system can be used to control the openings of the enclosure. This illustrates how to control one of the sources of sound radiation from the box.

Structural Radiation Only

The second source of transmission loss is provided by the structure of the box itself. The sound radiating from this box is due to the acoustical and hence, structural excitation provided by the distributed source. That is, the interior acoustic field and any structural attachments from the distributed source excite the structure of the box which then radiates sound to the far-field. A method of controlling the sound radiation from the box is to place acoustic sources within the box and controlling them with sensors which minimize: either:

1. The entire acoustical field within the box (such as a microphone within the box).
2. Only those acoustic modes within the box which effectively couple to the box's structure and consequently can be radiated by the structure into the far-field (telling the microphone within the box which frequencies have structural modes to control.
3. Sensing far-field noise and minimizing it utilizing the acoustic sources in the box. This can be done either with a number of microphones in the far-field, or, more preferably with a number of PVDF sensors on the surface of the box to measure the efficiently radiating modes. This embodiment will control only those interior acoustic modes which couple well with the efficiently radiating modes of the box structure.

Figure 2:
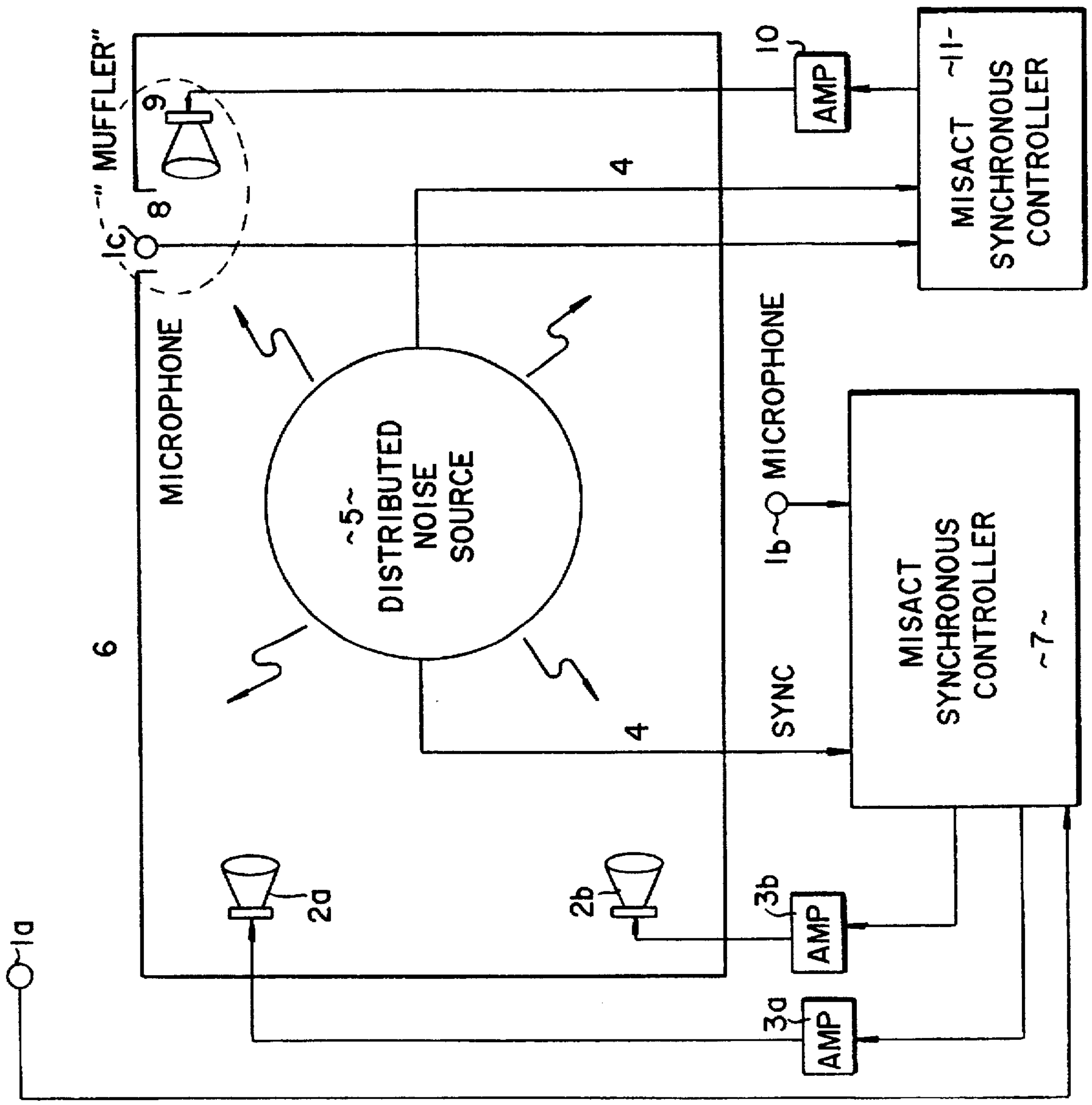
FIG. 2 is a variant of the enclosure of FIG. 1 using a MIMO (multiple input, multiple output) controller.

FIG. 2 shows the implementation of method (3).

The entire system can be controlled with a single MISACT (Multiple Sensors and Actuators, U.S. Pat. No. 5,091,953) which is hereby incorporated by reference herein, or other suitable MIMO controllers. The use of a microphone in the box to sense only the efficiently coupling modes is unique as is the use of far-field sensors for minimization using acoustic sources within the box is also unique. While to the untrained it may appear that this method is the equivalent of choosing only the efficiently radiating modes with the microphone in the box that is not the case. The set of interior acoustic modes which effectively couple to the box's efficiently radiating modes is probably smaller than the set of interior modes which effectively couple to the box's structural modes.

To control the sound radiation from openings an acoustic control system is employed for each opening. In this way there is not a complex control problem. This is possible because the control field in the interior of the box will combine with the noise from the distributed source and, being in the same frequency range, will be a compact source at the opening. It is possible to couple all of the sensors and acoustic sources together into a single MIMO controller.

A microphone in the box/enclosure is used as error sensor for a control algorithm. It is important to choose the proper bandwidth for control as the structure has some passive sound reduction characteristics which may or may not be close to the disturbance frequency. If a microphone is used in the enclosure, a filter for the microphone is ideally constructed to place all of the control effort in the portion of the disturbance spectrum that efficiently radiates to the far-field outside of the enclosure. This may or may not be the same as simply sensing all of the noise generated within the box. An effective way to achieve this type of filtering is to characterize the radiation characteristics of the enclosure, and construct a digital or analog filter with the proper characteristics. An additional way to achieve this type of filtering follows.

The use of a far-field sound sensor (outside of the structure of the box) is another method to properly filter the input to the active control system. It will functionally the same as "somehow" choosing only the efficiently radiating modes with the microphone in the box. Thus, by microphone placement, the proper filtering is achieved.

Combination of Structural Radiation and Airborne Radiation

In most practical cases requiring a sound enclosure, the enclosure must provide means for air flow (i.e. for internal combustion engines). This means that both airborne and structural radiation must be considered to effect the noise control. The two types of systems previously disclosed can be used in combination to provide noise control through both types of paths. Using a multi input/multi output active noise cancellation algorithm ( as in U.S. Pat. No. 4,878,188 herein incorporated by reference) all control sensors and actuators can be driven to minimize the overall sound radiation.

It is also possible to use a number of independent controllers to achieve similar results. In this way one will not have a very complex control problem. This is possible because the control field in the interior of the box will combine with the noise from the distributed source, and being in the same frequency range, will be a compact source at the opening. Thus, each opening could be controlled by a SISO controller, while a MIMO controller simultaneously controls the sound radiation from the structure.

The design of the openings of the box should be designed to have a high acoustical impedance in the control bandwidth of the interior speakers. This will allow the speakers to "appear" to drive into a closed volume, and hence smaller speakers can be used when compared to driving into free space. At the frequency of the airflow (DC or zero hertz) the openings will still have near zero loss. This is necessary for enclosing internal combustion engines.

Figure 4:
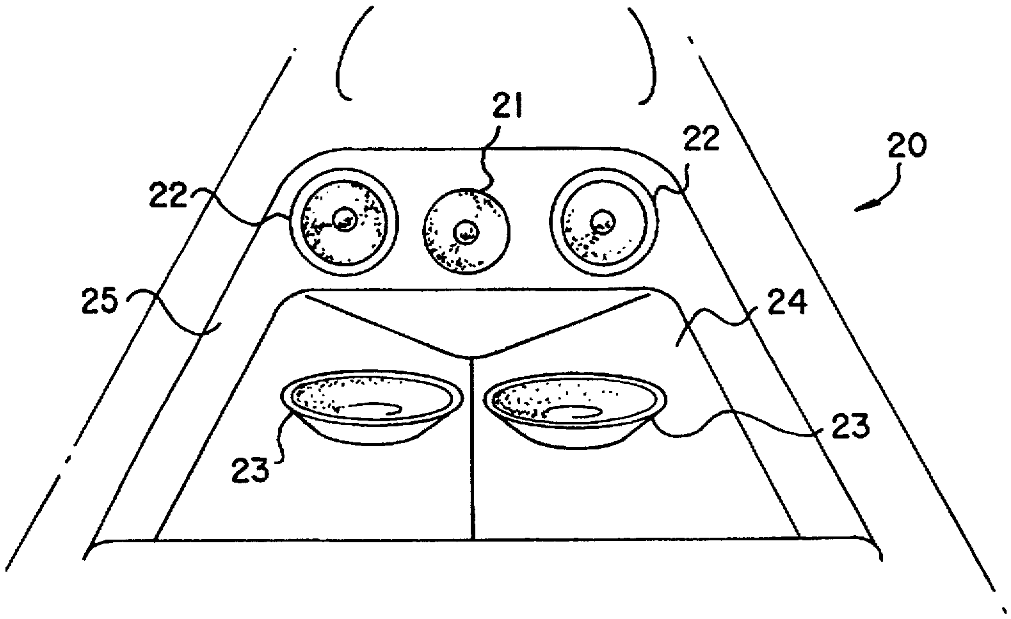
FIG. 4 is a perspective view of the engine compartment of a personal watercraft.

An example of an implemented active enclosure is shown in FIG. 4. A personal watercraft 20 with a two-stroke internal combustion engine was treated with control loudspeakers 22 within the engine compartment 25 with floor 24 in order to control structural sound radiation from the engine enclosure. An air inlet 21 for the engine compartment was designed to have a high acoustical impedance in the control bandwidth. A mock-up was created to test the system which was designed for the watercraft. The mock-up consisted of the empty hull of the craft and used two loudspeakers 23 to simulate the noise of the engine. The specially designed air inlet was installed in the mock-up as were the two controlling loudspeakers. The cover of the watercraft is shown off of the engine compartment.

A 200 Hz tone at approximately 110 dB SPL was played into the engine compartment with the corresponding inside and outside SPL spectrum shown in FIG. 5. This compares to a SPL of 114 dB recorded in the engine compartment with the engine running. The controller was turned on and the inside and outside spectra changed to that shown in Plot 2.

DETAILED DESCRIPTION OF FIGURES

FIG. 1 depicts a distributed noise source 5 surrounded by an enclosure structure 6 with an opening 8. Microphones **1*a*, 1*b* detect the sound within the enclosure structure which is then filtered 11*a*, 11*b* to focus the control effort of the loudspeakers 2*a*, 2*b* on that portion of the noise which radiates to the far field. Microphone 1*c* at the opening 8 is fed (with other appropriate signal conditioning) to the controller 7. The loudspeaker 9** controls the sound field exciting the opening.

The multiple input/multiple output controller 7 takes the microphone inputs and the sync signal 4 from the noisy equipment and creates an output signal to minimize the sound radiation. The necessary amplifiers **3*a*, 3*b*, 10** are utilized to drive the speakers.

The opening 8 is designed to have a high acoustic impedance in the frequency range of control.

FIG. 2 depicts a distributed noise source 5 surrounded by an enclosure structure 6 with an opening 8. Microphones **1*a*, 1*b* detect the sound radiated from the enclosure structure and feeds this input to MIMO controller 7. The controller creates a control signal which is then fed through the amplifiers 3*a*, 3*b* to the loudspeakers 2*a*, 2*b*. Microphone 1*c* at the opening 8 is fed (with other appropriate signal conditioning) to another controller 11. The loudspeaker 9 controls the sound field exciting the opening. The sync signal 4 is fed as an additional input to both controllers 7, 11**.

The multiple input/multiple output controller 7 takes the microphone inputs and the sync signal 4 from the noisy equipment and creates an output signal to minimize the sound radiation. The independent controller 11 is used to control the sound emanating from the opening 8.

The opening 8 is designed to have a high acoustic impedance in the frequency range of control.

Figure 3:
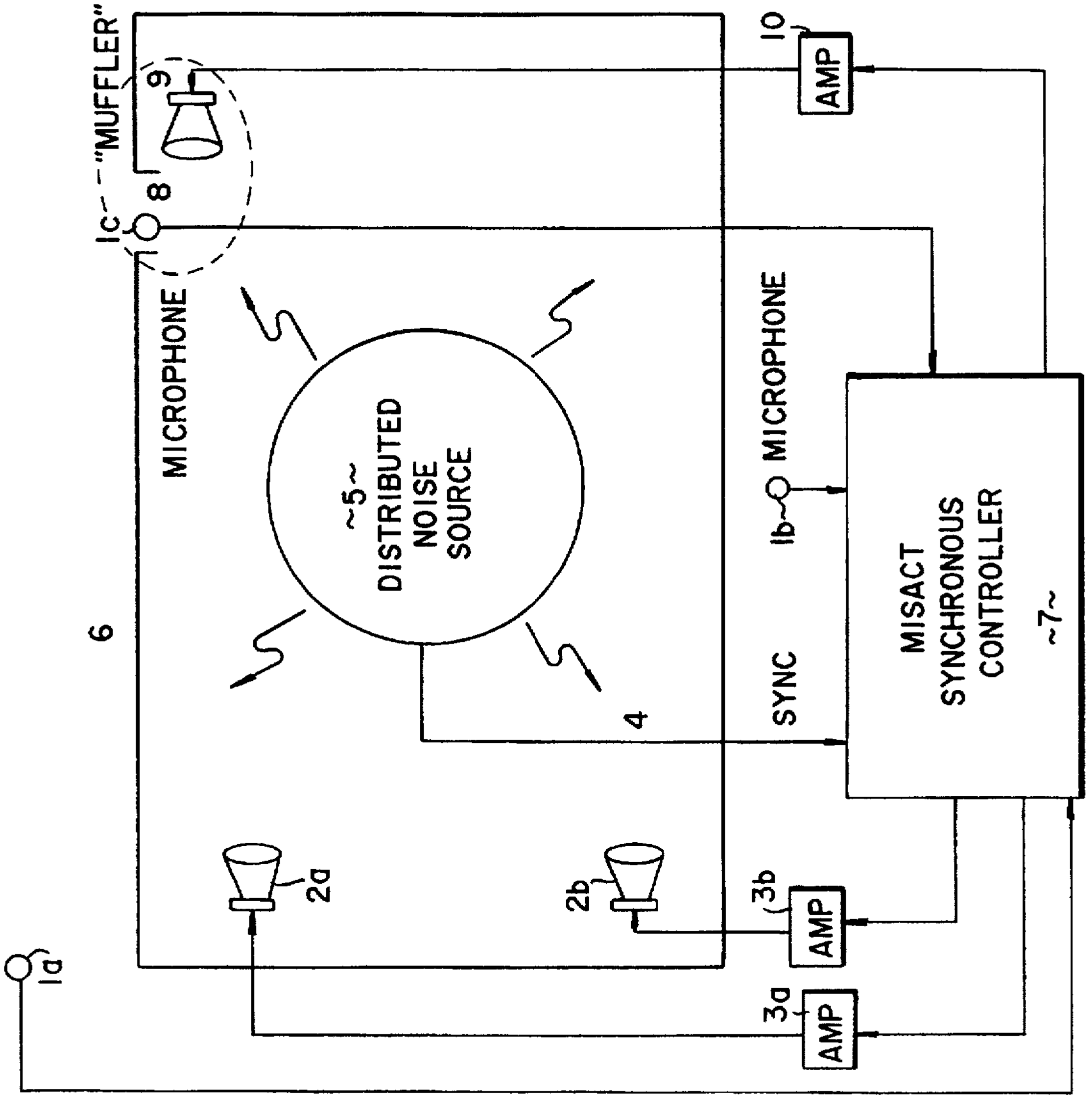
FIG. 3 is a distributed noise source surrounded by an enclosure.

FIG. 3 depicts a distributed noise source 5 surrounded by an enclosure structure 6 with an opening 8. Microphones **1*a*, 1*b*, 1*c* detect the sound radiating from the enclosure structure which is then fed to the controller 7 to focus the control effort of the loudspeakers 2*a*, 2*b* on that portion of the noise which radiates to the far field. Microphone 1*c* at the opening 8 is fed (with other appropriate signal conditioning) to the controller 7. The loudspeaker 9** controls the sound field exciting the opening.

The multiple input/multiple output controller 7 takes the microphone inputs and the sync signal 4 from the noisy equipment and creates an output signal to minimize the sound radiation. The necessary amplifiers **3*a*, 3*b*, 10** are utilized to drive the speakers.

The opening 8 is designed to have a high acoustic impedance in the frequency range of control.

Having described the preferred embodiment of the invention it will be obvious to those of ordinary skill in the art that changes and modifications can be made without departing from the scope of the appended claims.

I claim:

1. A system for actively acoustically attenuating noise radiating from a source within an enclosure, said system comprising:

first sensing means adapted to sense far-field noise external of said enclosure;

speaker means within said enclosure positioned so as to be able to actively attenuate said noise; and controller means adapted to produce counter noise in response to said sensed noise and cause said speaker means to actively counter said noise;

wherein said enclosure has no apertures therein and said sensing means is located external to said enclosure to sense the sound radiated from the enclosure structure.

2. A system for actively acoustically attenuating noise radiating from a source within an enclosure, said system comprising:

first sensing means adapted to sense far-field noise external of said enclosure;

speaker means within said enclosure positioned so as to be able to actively attenuate said noise; and controller means adapted to produce counter noise in response to said sensed noise and cause said speaker means to actively counter said noise:

wherein said enclosure has no apertures therein and said first sensing means is located within said enclosure and includes filter means associated with said sensing means and adapted to focus the control effort of said speaker means on that portion of the noise that radiates into the far-field.

3. A system for actively acoustically attenuating noise radiating from a source within an enclosure, said system comprising:

first sensing means adapted to sense far-field noise external of said enclosure;

speaker means within said enclosure positioned so as to be able to actively attenuate said noise; and controller means adapted to produce counter noise in response to said sensed noise and cause said speaker means to actively counter said noise;

wherein said enclosure has no apertures and said controller means utilizes a multiple input, multiple output algorithm control and there are at least two first sensing means.

4. A system as in claim 3 wherein said sensing means are located external of said enclosure and are microphones.

5. A system as in claim 3 wherein said sensors are located on the external surface of said enclosure and are PVDF sensors.

6. A system as in claim 3 wherein said sensors are adapted to be located within said enclosure and including filter means associated with said sensing means and adapted to focus the control effort of said speaker means on that portion of the noise that radiates into the far-field.

7. The system of claim 1, wherein said first sensing means are located on the external surface of said enclosure and are PVDF sensors.

8. The system of claim 1, wherein said first sensing means are located external of said enclosure and are microphones.

9. The system of claim 2, wherein said first sensing means are located on the external surface of said enclosure and are PVDF sensors.

10. The system of claim 2, wherein said first sensing means are located external of said enclosure and are microphones.

11. The system of claim 3, wherein said first sensing means are located on the external surface of said enclosure and are PVDF sensors.

12. The system of claim 3, wherein said first sensing means are located external of said enclosure and are microphones.

* * * * *